(12) United States Patent
Mas

(10) Patent No.: US 7,959,648 B2
(45) Date of Patent: Jun. 14, 2011

(54) DEVICE AND METHOD FOR EFFECTING HEMOSTASIS ABOUT A PUNCTURE

(75) Inventor: Juan-Pablo Mas, Somerville, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 559 days.

(21) Appl. No.: 12/107,186

(22) Filed: Apr. 22, 2008

(65) Prior Publication Data
US 2009/0264922 A1 Oct. 22, 2009

(51) Int. Cl.
*A61B 17/08* (2006.01)
(52) U.S. Cl. .................................................. 606/216
(58) Field of Classification Search .............. 606/213, 606/215–216, 219, 139, 144; 607/127, 128, 607/131; 600/217
See application file for complete search history.

(56) References Cited

U.S. PATENT DOCUMENTS

| | | | | | |
|---|---|---|---|---|---|
| 2,097,380 | A | * | 10/1937 | Morgan | 112/80.05 |
| 3,416,534 | A | * | 12/1968 | Quinn | 607/131 |
| 4,669,473 | A | | 6/1987 | Richards et al. | |
| 4,846,805 | A | * | 7/1989 | Sitar | 604/165.04 |
| 5,292,309 | A | * | 3/1994 | Van Tassel et al. | 604/117 |
| 5,431,649 | A | * | 7/1995 | Mulier et al. | 606/41 |
| 5,437,266 | A | * | 8/1995 | McPherson et al. | 600/217 |
| 5,454,834 | A | * | 10/1995 | Boebel et al. | 606/228 |
| 5,496,332 | A | * | 3/1996 | Sierra et al. | 606/139 |
| 5,573,540 | A | * | 11/1996 | Yoon | 606/139 |
| 5,700,273 | A | * | 12/1997 | Buelna et al. | 606/148 |
| 5,810,882 | A | * | 9/1998 | Bolduc et al. | 606/213 |
| 5,836,955 | A | * | 11/1998 | Buelna et al. | 606/148 |
| 6,117,144 | A | * | 9/2000 | Nobles et al. | 606/144 |
| 6,245,079 | B1 | * | 6/2001 | Nobles et al. | 606/144 |
| 6,391,048 | B1 | | 5/2002 | Ginn et al. | |
| 6,461,366 | B1 | | 10/2002 | Seguin | |
| 6,517,553 | B2 | * | 2/2003 | Klein et al. | 606/144 |
| 6,544,195 | B2 | * | 4/2003 | Wilson et al. | 600/564 |
| 6,767,356 | B2 | | 7/2004 | Kanner et al. | |
| 6,770,083 | B2 | * | 8/2004 | Seguin | 606/142 |
| 6,964,668 | B2 | * | 11/2005 | Modesitt et al. | 606/144 |
| 7,169,160 | B1 | | 1/2007 | Middleman et al. | |
| 2003/0105473 | A1 | * | 6/2003 | Miller | 606/139 |
| 2004/0147957 | A1 | * | 7/2004 | Pierson, III | 606/228 |
| 2004/0167546 | A1 | * | 8/2004 | Saadat et al. | 606/144 |
| 2006/0052821 | A1 | * | 3/2006 | Abbott et al. | 606/213 |
| 2006/0212071 | A1 | * | 9/2006 | Ginn et al. | 606/219 |
| 2006/0247644 | A1 | * | 11/2006 | Bhatnagar et al. | 606/75 |
| 2008/0097372 | A1 | * | 4/2008 | Shimizu et al. | 604/414 |
| 2008/0097523 | A1 | * | 4/2008 | Bolduc et al. | 606/219 |

FOREIGN PATENT DOCUMENTS

WO WO 03/090864 6/2003

* cited by examiner

Primary Examiner — Darwin P Erezo
Assistant Examiner — Son Dang

(57) ABSTRACT

A device and method for closing a percutaneous vascular puncture with anchors at the distal ends of wires temporarily implanted in extravascular tissue adjacent the puncture. The wires are tensioned to draw the tissue together to approximate the edges of the puncture. The wires are retained in that position while the blood in the region of the arteriotomy clots. When hemostasis has been achieved, the anchoring wires then can be removed.

15 Claims, 5 Drawing Sheets

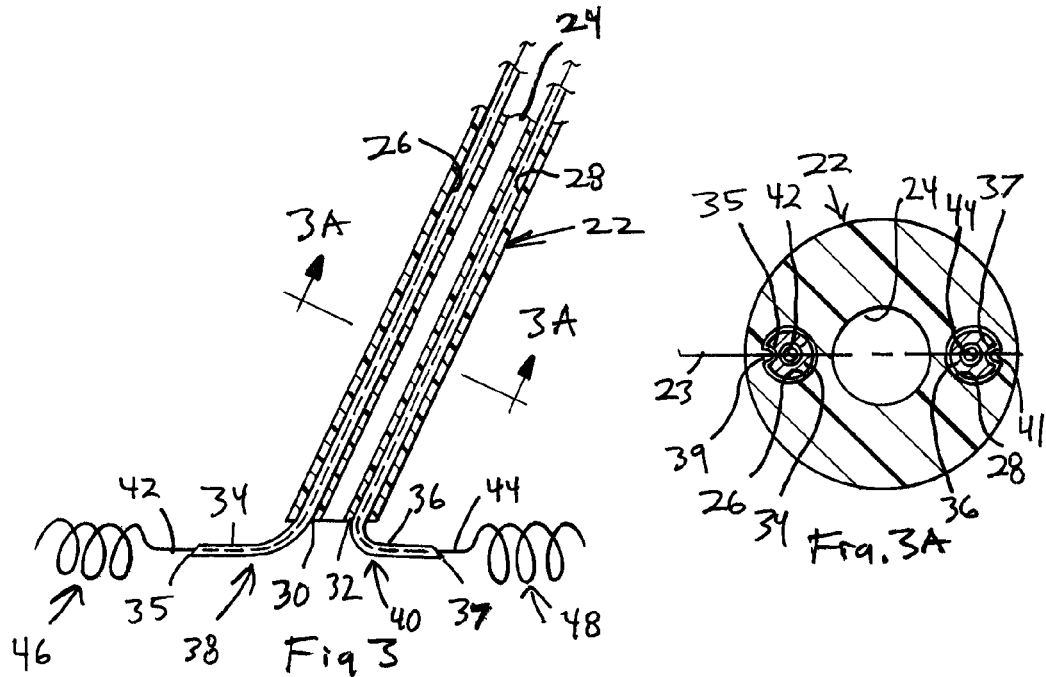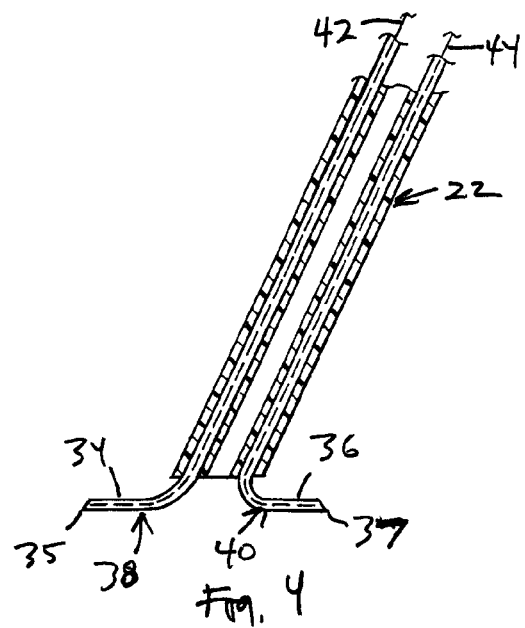

DEVICE AND METHOD FOR EFFECTING HEMOSTASIS ABOUT A PUNCTURE

FIELD OF THE INVENTION

The invention relates to devices and techniques for effecting hemostasis about a puncture in a blood vessel after an intravascular procedure.

BACKGROUND

Various cardiovascular procedures, such as angioplasty and stent placement among others, are performed by inserting into and manipulating within a patient's vasculature, wires and catheters adapted to perform those procedures. In coronary and other such vascular interventional procedures access to the vasculature typically is percutaneous, often through the femoral artery, involving insertion of a needle in the region of the groin to form a track through subcutaneous tissue and to puncture and create an arteriotomy in the artery. A short guidewire then is advanced through the needle and into the femoral artery. The needle then is removed and a dilator carrying an introducer sheath then is advanced over the guidewire, along the needle track and into the femoral artery. The dilator enlarges the track through the tissue and widens the puncture in the vessel so that it may receive subsequent guidewires, catheters and the like. With the introducer sheath having been advanced into the vessel, the dilator and short guidewire are removed leaving the sheath in place. The sheath provides access into the femoral artery, through the arteriotomy, for catheters or other instrumentalities in order to perform the selected procedure.

After the procedure has been completed, the procedural devices are removed and the arteriotomy must be closed. A number of techniques are known to facilitate closure and healing of the arteriotomy. These include application of pressure at the puncture site for a relatively extended length of time, or the use of biological adhesives or plugs adapted to seal the arteriotomy, or the use of staples or clips. Some closure systems include an arrangement to engage the artery to temporarily draw the edges of the arteriotomy together while a final closure device, such as a stapler, sutures, adhesives or other means is used to effect the permanent closure of the arteriotomy. Some of these systems result in piercing the vessel wall or other tissue, such as systems described, for example, in U.S. Pat. No. 6,767,356 (Kanner) and U.S. Pat. No. 6,391,048 (Ginn et al.).

It would be desirable to provide an alternate system for effecting hemostasis of a vascular puncture wound without risking the trauma that may result from piercing the vascular wall and also to avoid the risk of a closure element projecting into the interior of the vessel lumen. The present invention is directed to such an alternative device and technique.

SUMMARY OF THE INVENTION

The invention employs a percutaneously placeable closure device that can be advanced along a track or over an indwelling guidewire and by which tissue located close to, but exteriorly of, the blood vessel wall can be gripped on opposite sides of the puncture and then drawn together. Tissue immediately adjacent the blood vessel that is attached to the outer surface of the blood vessel thus may be drawn together to draw portions of the vessel wall toward each other. By engaging the tissue on opposite sides of and in close proximity to the puncture, the edges of the puncture can be approximated without piercing the vessel wall.

A device for implementing the invention may include a sheath that contains a pair of hollow needles having sharp distal tips and pre-curved distal ends that are sufficiently flexible that they can be straightened and withdrawn into receptive passages in an elongate delivery sheath. Each hollow needle contains a flexible wire having a distal end preformed with a shape capable of self-anchoring within tissue when deployed within the tissue. The wire and pre-formed distal anchoring shape are such that the distal end of the wire can be retracted into the lumen of its associated needle with the anchor portion assuming a straightened shape. The needles and sheath are arranged so that as the needles emerge from the distal end of the sheath they extend in opposite directions, preferably lengthwise of the blood vessel.

The device may be used by advancing the delivery sheath along a guidewire and/or the existing puncture track to position the distal end of the sheath proximal to the outer surface of the blood vessel in the region of the puncture wound. The distal end of the sheath may be positioned with respect to the vessel puncture by means of a blood marking tube having a distal blood marking port that, when entering the blood vessel, enables blood to flow through the tube to provide an indication to the clinician at the proximal end of the tube that the vessel has been reached. The distal end of the sheath and the blood marking port are associated to indicate when the distal end of the sheath is in the proper position. The needles then are advanced through the sheath and, as they emerge from their respective passages, will assume their curved configurations in opposite directions. Preferably the needles extend in approximately a common plane that extends longitudinally of the blood vessel and generally perpendicular to the orientation of the vessel puncture. Means are provided to guide the needles in that orientation. When the curved needles have been extended into the desired depth in the tissue and with the distal ends of the wires extending to the distal end of the needle lumens, the needles are retracted while the wires are maintained in place. As the needles retract, the distal ends of the wires are freed from the restraint of the needles and assume the pre-formed anchor configuration within the tissue. With the anchors secured to the tissue, the wires then are tensioned to draw the tissue together that, in turn, draws the edges of the vessel puncture together. The wires are retained in that position while the blood in the region of the arteriotomy clots, resulting in hemostasis. External pressure also may be applied, as by manual compression, for example. When hemostasis has been achieved, the anchoring wires then can be removed by re-advancing the needles distally over the extended wires. As the needles advance over the wires, the anchor configurations are straightened and recaptured into the needle lumens. The device then may be withdrawn from the patient.

DESCRIPTION OF THE DRAWINGS

The foregoing and other features and advantages of the present disclosure will be apparent from the following description of the disclosure as illustrated in the accompanying drawings. The accompanying drawings, which are incorporated herein and form a part of the specification, further serve to explain the principles of the disclosure and to enable a person skilled in the pertinent art to make and use the disclosure. The drawings are not to scale. In the accompanying drawings:

FIG. 3 is a diagrammatic illustration of the distal end of a closure device as may be used in the practice of the invention, with the needles extended out of the sheath and the and wires extended out of the needles;

FIG. 3A is a diagrammatic sectional illustration of the closure device as seen along the line 3A-3A of FIG. 3;

FIG. 4 is a diagrammatic illustration of the closure device in a configuration in which the needles are extended and with the wires contained within the needle lumens;

DESCRIPTION OF THE ILLUSTRATIVE EMBODIMENTS

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
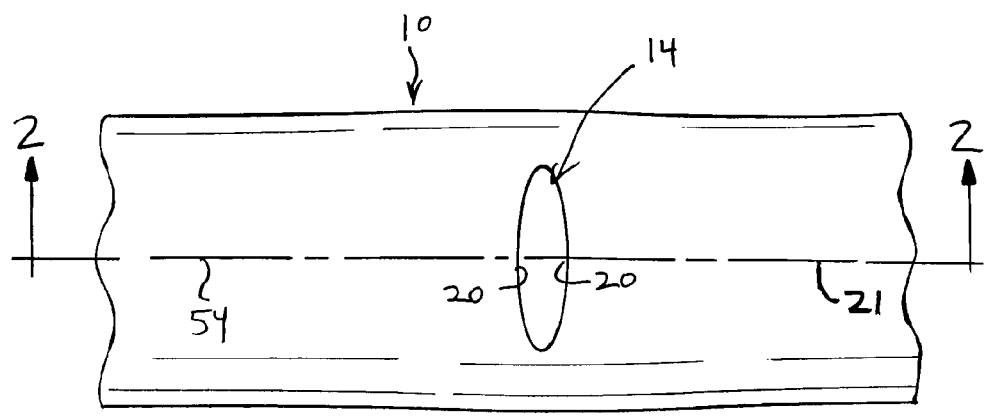
FIG. 1 is a diagrammatic illustration, in plan, of a blood vessel with a puncture wound.
Figure 2:
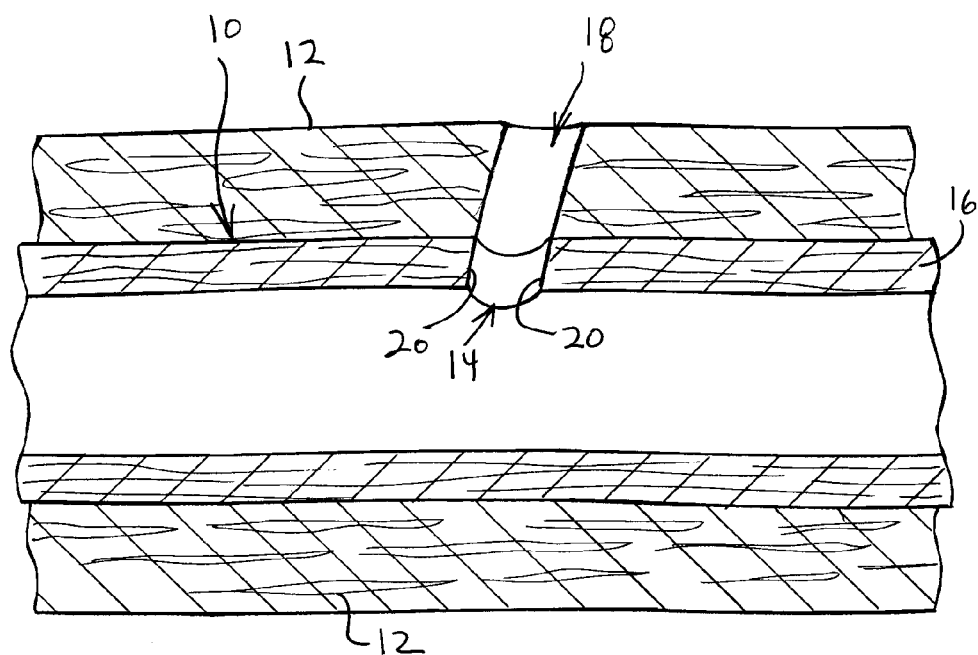
FIG. 2 is a diagrammatic sectional illustration of the arteriotomy and surrounding tissue as seen along the medial plane 2-2 of FIG. 1.

FIGS. 1 and 2 illustrate, diagrammatically, a blood vessel 10 and surrounding tissue, indicated diagrammatically at 12, through which the vessel has been accessed percutaneously. The anatomy of arteries is such that when an artery is pierced by a needle, dilator or catheter, the puncture 14 that is formed is in the form of a circumferentially extending slit, a consequence of the circumferential orientation of the muscle fibers within the wall 16 of the vessel. As various sheaths and catheters are inserted percutaneously through the arteriotomy, the region of the arteriotomy is stretched to accommodate these devices. These devices also form a track 18 through the skin and tissue 12 leading to the vessel puncture 14.

After the vascular procedure has been completed, the procedural devices are removed and the arteriotomy must be closed. The present invention employs a technique in which the edges 20 of the arteriotomy 14 are drawn together by engaging and drawing together tissue 12 that is external of and adjacent to the vessel wall in the region of the arteriotomy. That adjacent tissue may be comprised of fascia, membranes such as the femoral sheath, and fatty tissue. The tissue immediately adjacent the outer surface of the vessel often is attached to the vessel wall sufficiently so that the tissue, which had been separated to form the track along which the needles, guidewires, dilators and catheters were advanced, can be drawn together. The present invention employs an arrangement by which such extravascular tissue 12 can be engaged and drawn together, thus drawing together the edges 20 of the arteriotomy to which the extravascular tissue is attached.

Figure 5:
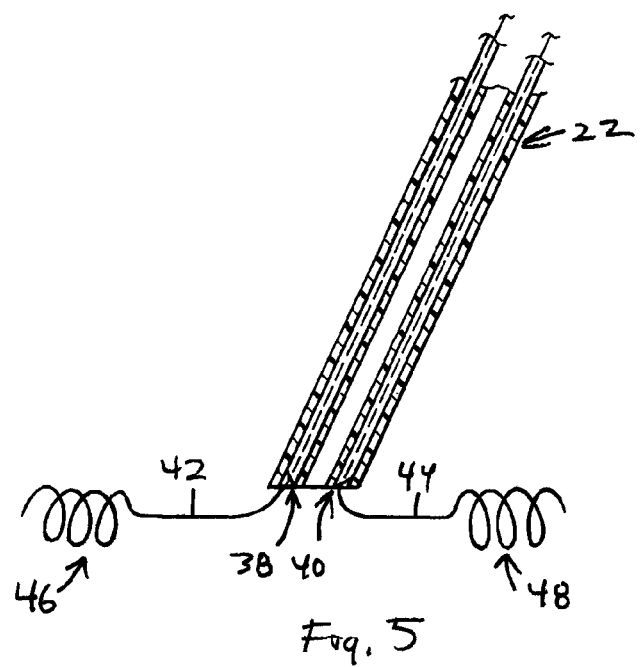
FIG. 5 is a diagram of the closure device with the needles retracted into the sheath and the wires extended, showing the distal ends of the wires formed to define anchoring elements.

FIGS. 3-5 illustrate, diagrammatically and in different stages of deployment, the components of an illustrative embodiment of the invention. The arrangement includes a delivery sheath 22 having a central passage 24 and a pair of needle passages 26, 28 extending therethrough. Each of the needle passages 26, 28 terminates in a distal outlet port 30, 32, respectively. As shown in FIG. 3A the central passage 24 and needle passages 26, 28 preferably are arranged in alignment such that they extend along a common medial plane 23 of the sheath. In practicing the invention it is desired to orient the shaft with respect to a medial plane 21 (FIG. 1) of the blood vessel and tissue track 18 so that the medial planes 21, 23 coincide or are closely parallel to each other. In order for the sheath 22 to be positioned in the desired orientation about its longitudinal axis, the sheath and/or a control handle at the proximal end of the device may be provided with visual indicia (not shown) by which the clinician can determine the proper rotational orientation of the sheath about its axis. Such visual indicia may be in the form of a marking or visually distinguishable device component that lies along or is perpendicular to the medial plane 23 of the device.

Hollow needles 34, 36 are contained slidably within the passages and are guided so that they can emerge from the distal ports 30, 32 and extend in diametrically opposite directions. The distal ends 38, 40 of the needles 34, 36 are preformed so that when unconstrained, they will assume a selected curved configuration. The needles may be formed from nitinol hypotubing and, for example, may have an outer diameter of between about 0.020 inch to about 0.030 inch with a wall thickness of about 0.005 inch. The curved configuration at the distal end of the needles should be such that when the needles have curved so that their distal tips extend in forward and rearward directions, generally paralleling the vessel, they have penetrated the tissue to a sufficient depth to facilitate placement of the anchors, as described below. By way of example, the distal tips of the needles may penetrate into the tissue of the order of about ⅜ to ⅝ inch.

In order to guide the emerging needles in opposite directions along the medial planes 21, 23, the needles and needle passages are provided with guides. To this end, the needles 34, 36 may be formed to include a longitudinally extending groove in the wall of each needle. Such grooves may be formed by stamping or roller swaging or by other techniques known to those familiar with the art of hypotube manufacture or similar small tube manufacture. The sheath 22 may be provided, within each of the needle passages 26, 28, with elongate ribs 39, 41 adapted to engage the grooves in the respective needles. In the present example, elongate ribs 39, 41 extend along the medial plane 23, but the ribs may be positioned at any radial location around the needle passages 26, 28. The ribs 39, 41 may be formed continuously along the inner diameter of the needle passages 26, 28 or may be in the form of a projection at the distal end of each needle passage shaped and oriented to engage the needle grooves as they emerge from their respective lumens. In an alternative embodiment (not shown), the needles 34, 36 may be formed to have longitudinally extending ribs and the needle passages 26, 28 may have elongate groves adapted to engage the ribs on the respective needles. In another embodiment (not shown), the needles 34, 36 may be formed with a non-circular cross-sectional shape, such as an oval or polygon, and the needle passages 26, 28 may have a similar non-circular cross-sectional shape adapted to engage and guide the emerging needles in opposite directions along the medial planes 21, 23.

Delivery sheath 22 may be made from a unitary plastic extrusion having the desired profile to provide central passage 24 and needle passages 26, 28. Some examples of suitable biocompatible thermoplastics for melt-extruding sheath 22 are high density polyethylene (HDPE), rigid polyethylene block amide copolymer (PEBA), and fluoroethylene-propylene (FEP). Polytetrafluoroethylene (PTFE) resin is also an example of a material suitable for paste or "cold" extrusion of sheath 22. Alternatively, sheath 22 made be made of discrete tubes for providing central passage 24 and needle passages 26, 28, the tubes being bundled and held together by polymer tubing shrink-fitted around the tubes. Each of the discrete tubes can be made from metal tubing, e.g., nitinol or stainless steel, or from a suitable polymer. The exterior surface of sheath 22 need not be cylindrical.

FIG. 3 also illustrates a pair of wires 42, 44 associated respectively, with each of the needles 34, 36 with the distill ends of the wires being unconstrained and assuming their anchor configurations indicated generally at 46, 48. In the illustrative embodiment, the anchors 46, 48 may be in the form of a helical coil, as shown, although any other configuration capable of self-anchoring in tissue while also being able to be withdrawn back into the lumen of its associated needle may be suitable, including such wireforms as a curlicue or pigtail shape. The wires 42, 44 preferably are formed from nitinol and, in the illustrative embodiment, may have a diameter of between about 0.010 to about 0.020 inch.

Figure 7:
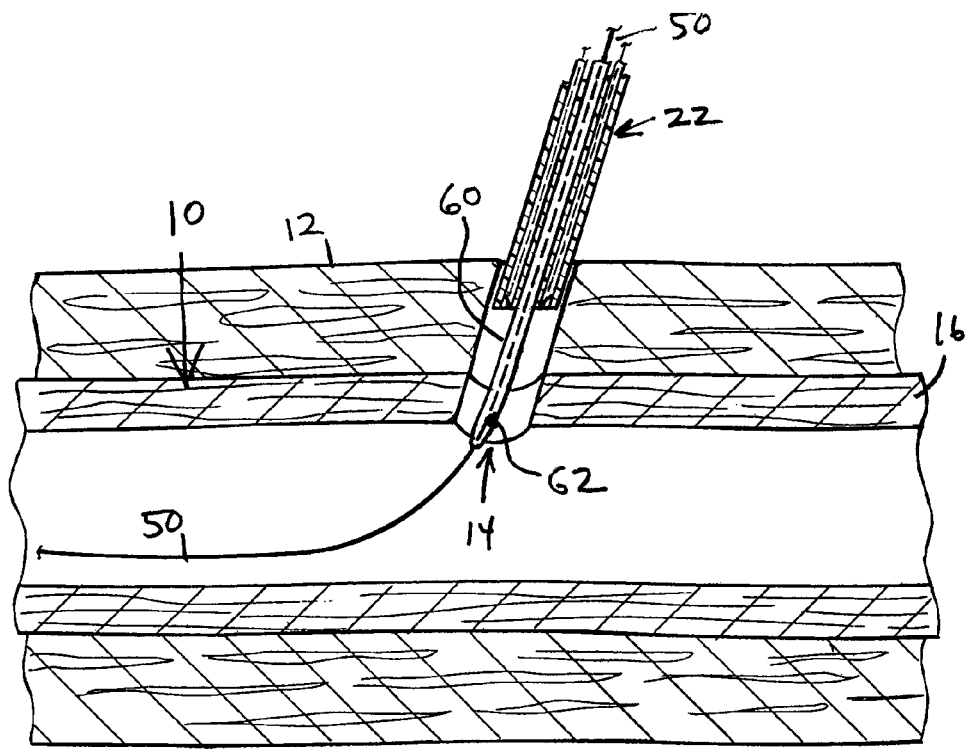

In order to position the distal end of the sheath at the desired depth within the tissue track 18, a blood marking tube 60 may be employed as shown in FIG. 7. The blood marking tube 60 extends through the central passage 24 and has a guidewire lumen by which the assembly can be tracked over an indwelling guidewire 50. The blood marking tube has a distal port 62 and a proximal port (not shown) that may be connected either by the guidewire lumen or by a separate lumen in the blood marking tube 60 by which entry of the distal tip into the vessel lumen can be determined at the proximal end of the tube. The longitudinal positions of the blood marking tube 60 and the sheath 22 are fixed so that when the distal end of the blood marking tube reaches the lumen of the blood vessel, that will be apparent from the presence or effluence of blood at the proximal end of tube 60. The distance between the distal blood marking port 62 and the distal end of the sheath 22 are predetermined to position the distal end of the sheath at the desired depth within the extravascular tissue 12.

Figure 6:
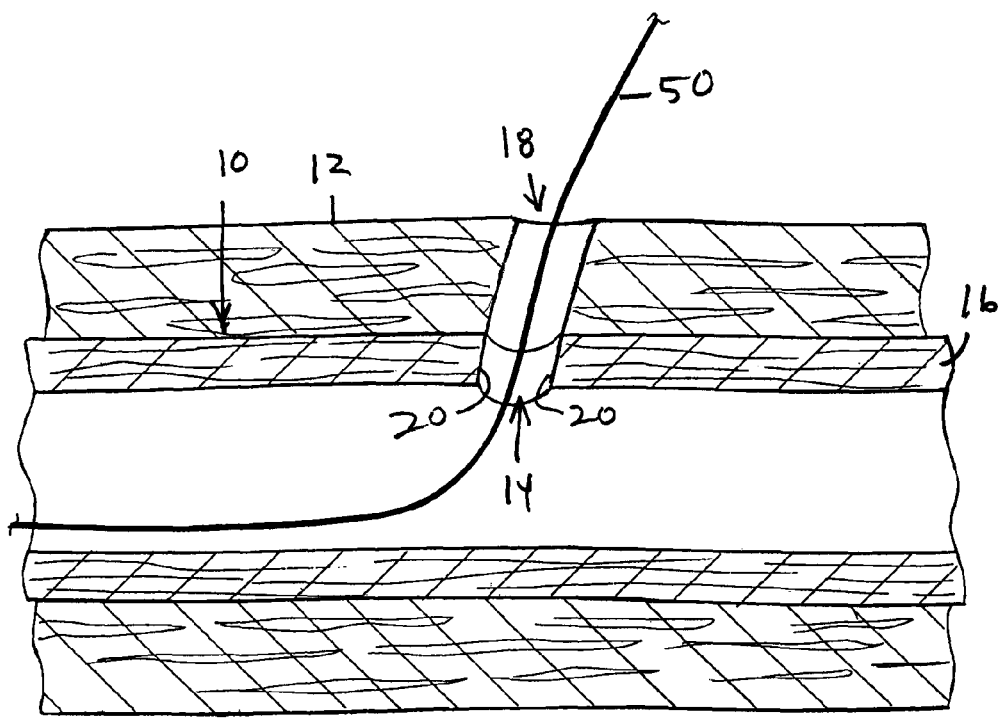
FIGS. 6-10 illustrate, diagrammatically, the sequence of steps as may be employed in practicing the invention with the illustrative closure device.
Figure 8:
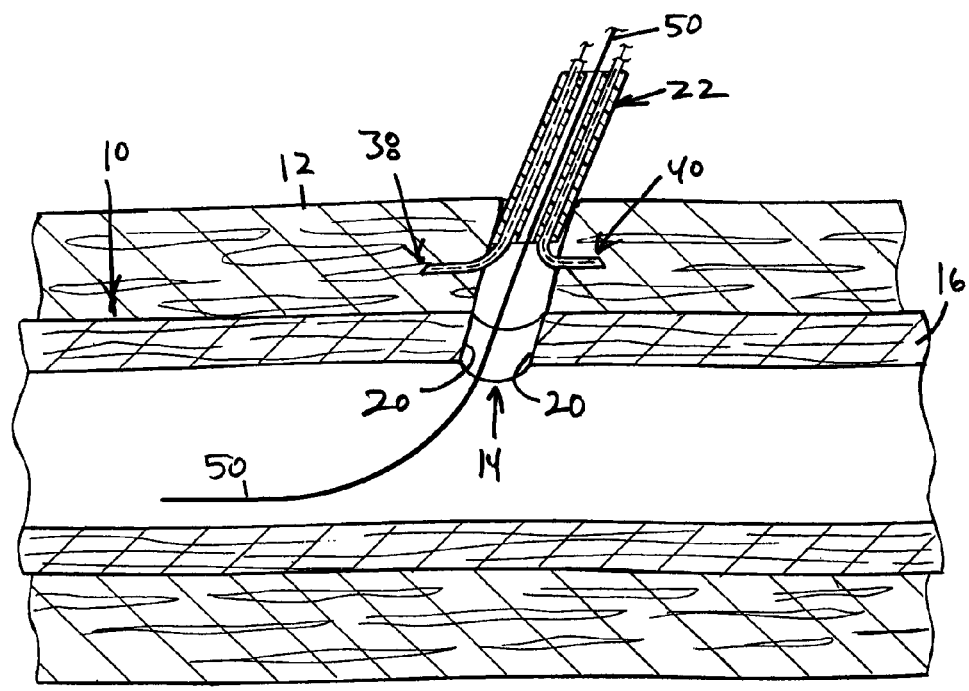
Figure 9:
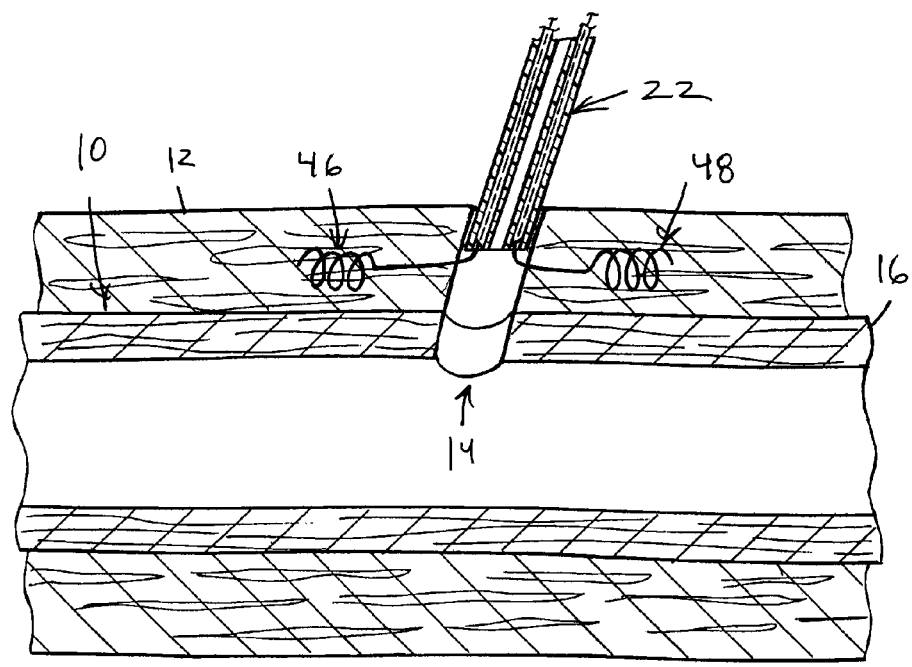

FIGS. 6-10 illustrate, diagrammatically, the manner in which the invention may be used. After the intravascular procedure (e.g., angioplasty, stent placement, etc.) has been concluded, the procedural catheters are removed. The indwelling guidewire 50 may be left in place to provide a guide for the puncture closure device (FIG. 6). It could be removed, however, allowing the device to be guided by the tissue track 18. The closure device of the invention is provided with the wires 42, 44 retracted within their associated hollow needles 34, 36 and the needles are retracted within their associated needle passages 26, 28 of the sheath 22. With the blood marking tube in position through the central passage 24, the distal end of the guidewire lumen of the blood marking tube is loaded onto the proximal end of the guidewire 50 extending externally of the patient and the assembly is advanced to the site of the arteriotomy (FIG. 7). When blood has appeared at the proximal port of the blood marking tube, indicating to the clinician that the distal end of the assembly has reached its intended location, and with the rotational orientation of the device such that the medial planes 21, 23 are in general alignment to properly orient the needle ports 30, 32, the needles 34, 36 are advanced distally within needle passages 26, 28 to cause their distal ends 38, 40 to emerge from the ports 30, 32. As the needles assume their pre-curved configurations, the sharp tips 35, 37 of the needles extend in opposite direction into the tissue disposed about the vessel puncture (FIG. 8). The needle tips thus are advanced to engage tissue 12 attached to portions of the vessel wall on opposite sides of the arteriotomy.

When the needles are embedded within extravascular tissue associated with opposite sides of the arteriotomy, the wires associated with the needles are advanced, if not already in position, until their distal ends extend to the tips of the needles (FIG. 4). While so positioned in the needles 34, 36, the distal ends of the wires are constrained in a generally linear or straight non-anchoring configuration. In order to deploy the wires to their respective distal anchor configurations 46, 48, the wires 42, 44 are maintained in position with respect to the sheath 22 while the needles 34, 36 are withdrawn back into the sheath 22 through the needle ports 30, 32. The distal ends of the wires will assume their anchor configurations 46, 48 as the needles are withdrawn, removing the constraining force about the wires. In an alternative manner in which the invention may be used, in order to deploy the wires to their respective distal anchor configurations 46, 48, the needles 34, 36 are maintained in position with respect to the sheath 22 while the wires 42, 44 are extended from the needle tips. The distal ends of the wires will penetrate extravascular tissue and assume their anchor configurations 46, 48. Then the wires 42, 44 are maintained in position with respect to the sheath 22 while the needles 34, 36 are withdrawn back into the sheath 22 through the needle ports 30, 32.

Figure 10:
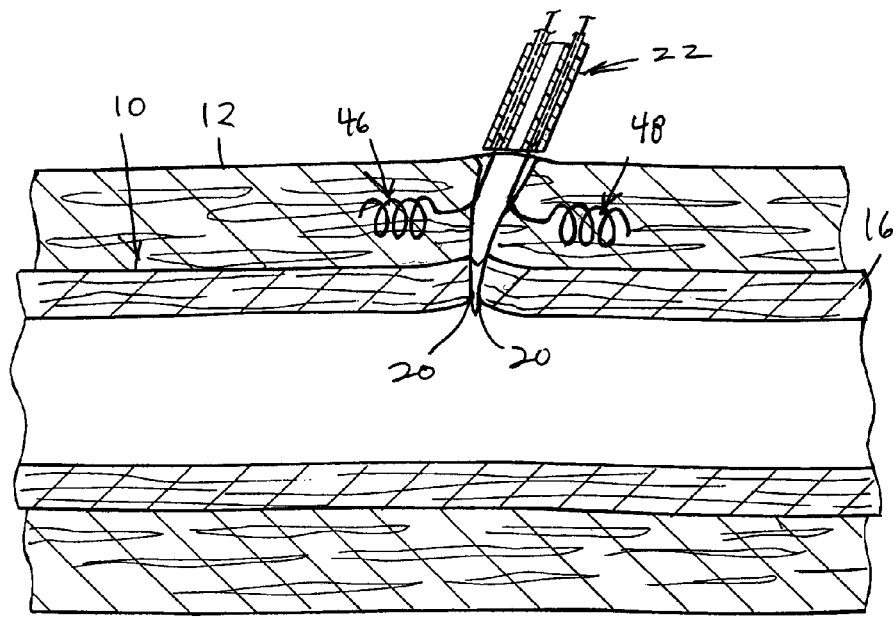

After the ends of the wires assume their anchor configuration secured within the tissue on opposite sides of the arteriotomy (FIG. 9), the wires 42, 44 then are drawn proximally toward the distal ends of the retracted needles, thus drawing together the anchors and the tissue 12 to which the wires are anchored (FIG. 10). The edges 20 of the arteriotomy 14 are drawn toward each other together with the tissues. The relative position of the wires, needles and sheath then are secured for a time sufficient to enable clotting and hemostasis to develop at the region of the tissue, vessel and arteriotomy. External pressure may be applied during this time, as by manual compression applied to the tissue 12 surrounding tissue track 18, to enhance the procedure. When it is determined that hemostasis has been completed, the needles are again deployed, this time to recapture the wires (FIG. 4). The configuration of the anchors should be such as to facilitate the recapture of the wires by advancing of the needles over the wires, progressively causing the wires to be straightened as they are engaged by the needle tips. When the needles have recaptured the wires, the needles are retracted in the sheath together with the wires and the device may be removed.

It should be understood that the foregoing description of the invention is intended merely to be illustrative thereof and that other embodiments, modifications and equivalents may be apparent to those skilled in the art while remaining within the scope of the invention. Although the apparatus of the invention has been described above as having only one pair of needles 34, 36 containing wires 42, 44, the invention is not so limited. Thus, the invention may incorporate more than two needles and a corresponding number of wires, arranged such that the plurality of needles emerges from the delivery sheath and places the wire anchors in a pattern for drawing together the intravascular tissue adjacent the vascular puncture.

The invention claimed is:

1. A medical apparatus comprising:
   an elongate sheath having at least three passages including a central passage and a pair of needle passages;
   a hollow needle slidably disposed within each needle passage, a distal tip of each needle being sharp for embedment in tissue, and a distal end of each needle being pre-formed to assume a predetermined curved shape when relaxed, the needles being extendable distally from and retractable into their respective needle passages;

the needles and sheath being cooperatively arranged to direct the needles in diametrically opposite directions when the needles are extended from their respective needle passages; and a wire slidably disposed within a lumen of each needle, each wire having a distal end with a pre-formed shape, the wire distal end having a straightened shape different from the pre-formed shape when constrained within the needle and being adapted to assume its pre-formed shape when extended distally beyond the distal end of the needle, the pre-formed shape defining an anchor adapted to securely engage tissue when assuming the pre-formed shape within tissue.

2. The apparatus as defined in claim 1 wherein the passages are aligned along a medial plane of the sheath.

3. The apparatus as defined in claim 2 further comprising:
cooperative guides associated with the needles and their respective needle passages to prevent the needles from rotating within their respective passages.

4. The apparatus as defined in claim 3 wherein the cooperative guides are oriented to guide the distal ends of the needles along the medial plane.

5. The apparatus as defined in claim 4 wherein the cooperative guides comprise:
each needle being provided with an external longitudinal groove and each needle passage being associated with a projection, the needle groove and needle passage projection being arranged to cooperatively mate to prevent rotation of the needle within the passage but to enable the needle to advance longitudinally out of the needle passage.

6. The apparatus as defined in claim 5 wherein the needle grooves and needle passage projections extend along the medial plane.

7. The apparatus as defined in claim 2 further comprising a blood marking tube disposed within the central sheath passage, the blood marking tube having a distal blood marking port, the tube having a maximum distal position with respect to the sheath, the distance between the distal blood marking port and the proximal end of the sheath being selected to position the distal end of the sheath within extravascular tissue.

8. The apparatus as defined in claim 1 wherein the pre-formed shape of each wire distal end is a helical coil.

9. The apparatus as defined in claim 1 wherein the pre-formed shape of each wire distal end is a curlicue.

10. The apparatus as defined in claim 1 wherein the pre-formed shape of each wire distal end is a pigtail.

11. A method for effecting hemostasis about a puncture surrounded by tissue, the method comprising:
providing an elongate sheath having a pair of needles slidably disposed in a corresponding pair of needle passages, each needle having a lumen therethrough terminating in an open distal end and a sharp distal tip for embedment in tissue, a flexible wire disposed in the lumen of each needle with each wire having a distal end disposed at the region of the distal end of the needle, the distal end of each wire being pre-formed into the shape of an anchor when unconstrained by the needle and being in a straightened shape different from the pre-formed shape when constrained within the needle;

locating a distal end of the sheath in proximity to the puncture;

advancing the needles out of their passages and directing the needles in diametrically opposite directions into the tissue, to pierce the tissue on opposite sides of the puncture;

delivering the wire distal ends from the needle distal ends to allow the anchors to form within the tissue to securely engage the tissue;

withdrawing the needles into their passages and urging the wires into the needles, thereby drawing the anchors together to draw the tissue together, thereby drawing the edges of the puncture toward each other; and maintaining the position of the anchors until hemostasis is achieved.

12. The method as defined in claim 11 wherein delivering the wire distal ends from the needle distal ends further comprises maintaining the position of the wires while withdrawing the needles over the wires.

13. The method as defined in claim 11 wherein delivering the wire distal ends from the needle distal ends further comprises maintaining the position of the needles while advancing the wire distal ends out of the needle distal ends.

14. The method as defined in claim 11 further comprising:
orienting the needles so that they are disposed along a medial plane of a blood vessel before the needles are withdrawn from the tissue.

15. The method as defined in claim 11 further comprising:
after hemostasis is achieved, advancing the needles out of their passages and recovering the wire distal ends into the needles to disengage the anchors from the tissue; and
removing from the tissue the sheath and the needles and the wires.

* * * * *